US012394246B2

(12) United States Patent
Tsuji et al.

(10) Patent No.: US 12,394,246 B2
(45) Date of Patent: Aug. 19, 2025

(54) EMOTION DETERMINATION DEVICE AND EMOTION DETERMINATION METHOD

(71) Applicant: OMRON Corporation, Kyoto (JP)

(72) Inventors: Ayana Tsuji, Kyoto (JP); Takashi Ohta, Kyoto (JP); Kazuya Urabe, Kyoto (JP); Tatsuki Sawada, Kyoto (JP)

(73) Assignee: OMRON CORPORATION, Kyoto (JP)

( * ) Notice: Subject to any disclaimer, the term of this patent is extended or adjusted under 35 U.S.C. 154(b) by 407 days.

(21) Appl. No.: 18/000,204

(22) PCT Filed: May 19, 2021

(86) PCT No.: PCT/JP2021/019006
§ 371 (c)(1),
(2) Date: Nov. 29, 2022

(87) PCT Pub. No.: WO2021/261126
PCT Pub. Date: Dec. 30, 2021

(65) Prior Publication Data
US 2023/0206691 A1 Jun. 29, 2023

(30) Foreign Application Priority Data
Jun. 24, 2020 (JP) .................................. 2020-108400

(51) Int. Cl.
*G06V 40/16* (2022.01)
*G06V 10/80* (2022.01)
*H04N 23/23* (2023.01)

(52) U.S. Cl.
CPC ............ *G06V 40/176* (2022.01); *G06V 10/80* (2022.01); *H04N 23/23* (2023.01)

(58) Field of Classification Search
None
See application file for complete search history.

(56) References Cited

U.S. PATENT DOCUMENTS

| 9,983,670 B2* | 5/2018 | Coleman ................ A61B 5/369 |
| 2003/0088367 A1* | 5/2003 | Kim ........................ G06N 3/004 |
| | | 702/19 |

(Continued)

FOREIGN PATENT DOCUMENTS

| CN | 109036405 A | 12/2018 |
| JP | 2009087074 A | 4/2009 |

(Continued)

OTHER PUBLICATIONS

Khan et al., "Toward Use of Facial Thermal Features in Dynamic Assessment of Affect and Arousal Level," IEEE Transactions on Affective Computing, vol. 8, No. 3, Jul.-Sep. 2017 (Year: 2017).*

(Continued)

*Primary Examiner* — Soo Shin
(74) *Attorney, Agent, or Firm* — ROSSI, KIMMS & McDOWELL LLP

(57) ABSTRACT

An emotion determination device includes a first estimator that estimates an emotion of a user based on a change in a facial expression of the user detected from a face image of the user, a second estimator that estimates the emotion of the user based on a change in a temperature of the user detected contactlessly from the user, and a determiner that determines the emotion of the user based on an estimation result obtained by the first estimator and an estimation result obtained by the second estimator.

11 Claims, 12 Drawing Sheets

(56) References Cited

U.S. PATENT DOCUMENTS

| | | | |
|---|---|---|---|
| 2011/0144804 A1 | 6/2011 | Song et al. | |
| 2015/0186912 A1* | 7/2015 | el Kaliouby | A61B 5/1128 382/218 |
| 2017/0105662 A1* | 4/2017 | Silawan | A61B 5/14542 |
| 2019/0355351 A1* | 11/2019 | Kim | G10L 15/22 |
| 2020/0104670 A1* | 4/2020 | Seo | G06V 40/174 |
| 2020/0150647 A1* | 5/2020 | Haneda | G05D 1/005 |
| 2021/0153752 A1* | 5/2021 | Park | A61B 5/0205 |

FOREIGN PATENT DOCUMENTS

| | | |
|---|---|---|
| JP | 2012059107 A | 3/2012 |
| JP | 2014178970 A | 9/2014 |
| JP | 2017144222 A | 8/2017 |
| JP | 2020068973 A | 5/2020 |
| KR | 1020140062917 A | 5/2014 |

OTHER PUBLICATIONS

International Search Report issued in Intl. Appln. No. PCT/JP2021/019006 mailed Jul. 27, 2021. English translation provided.
Written Opinion issued in Intl. Appln. No. PCT/JP2021/019006 mailed Jul. 27, 2021. English translation provided.
Office Action issued in Chinese Appln. No. 202180039522.0 mailed May 30, 2025.

* cited by examiner

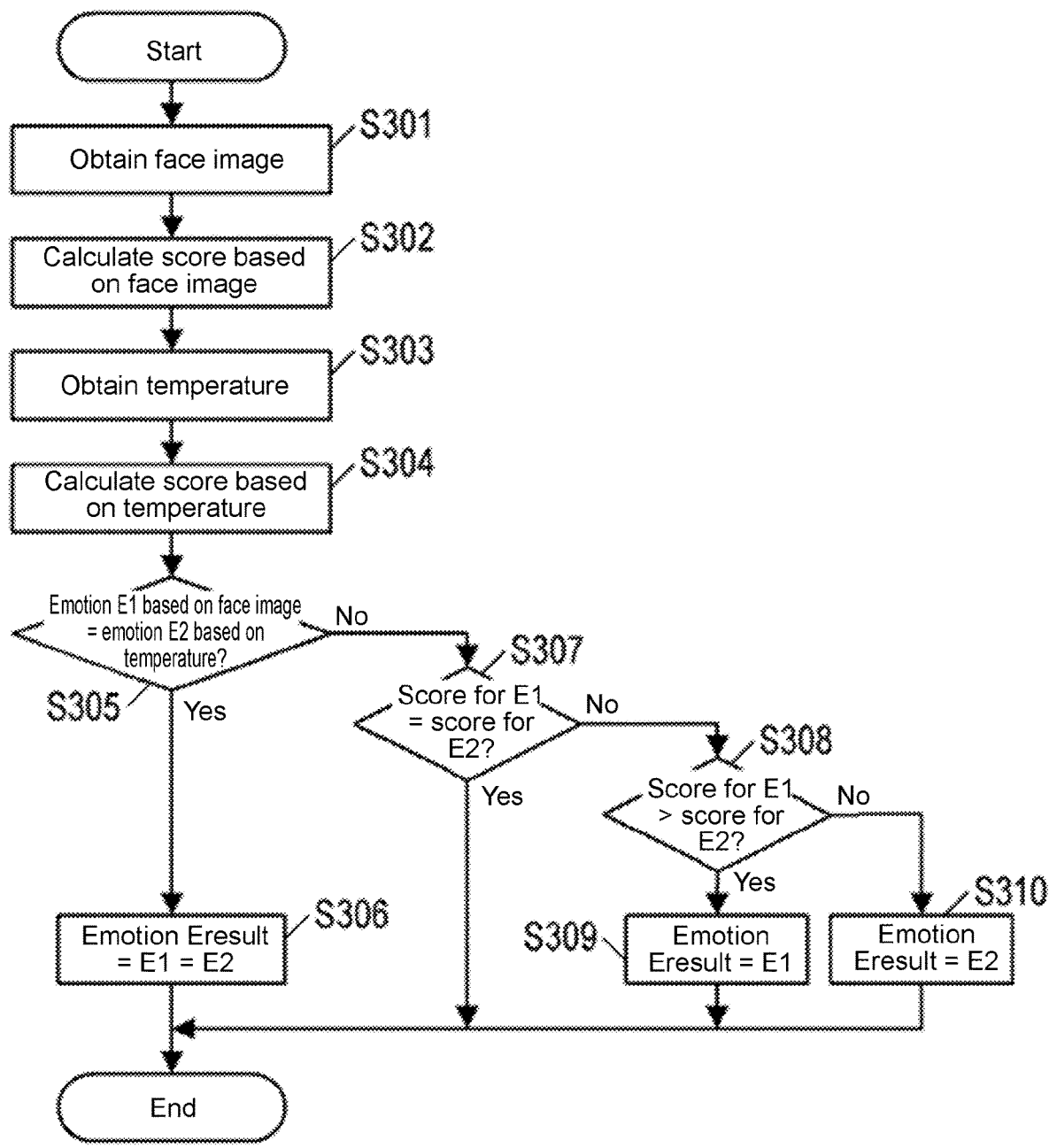

Temporal change of score based on facial image
(change in facial expression)

| Frame | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Calmness | 60 | 50 | 56 | 22 | 18 | 10 | 10 | 11 | 15 | 17 | 18 | 0 | 5 | 7 | 3 |
| Anger | 10 | 20 | 23 | 55 | 60 | 80 | 82 | 75 | 55 | 28 | 22 | 20 | 10 | 13 | 12 |
| Sadness | 10 | 20 | 11 | 12 | 12 | 5 | 5 | 10 | 25 | 55 | 60 | 80 | 83 | 75 | 80 |
| Joy | 20 | 10 | 10 | 11 | 10 | 5 | 3 | 4 | 5 | 0 | 0 | 0 | 2 | 5 | 5 |

Temporal change of score based on temperature
(change in temperature)

| Frame | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Calmness | 60 | 59 | 61 | 52 | 50 | 25 | 15 | 9 | 5 | 17 | 18 | 12 | 23 | 25 | 7 |
| Anger | 5 | 10 | 10 | 20 | 30 | 50 | 65 | 80 | 75 | 55 | 50 | 20 | 10 | 5 | 10 |
| Sadness | 10 | 8 | 9 | 8 | 10 | 10 | 10 | 6 | 15 | 18 | 23 | 55 | 62 | 65 | 78 |
| Joy | 25 | 23 | 20 | 20 | 10 | 15 | 10 | 5 | 5 | 10 | 9 | 13 | 5 | 5 | 5 |

Temporal change of determined emotion

FIG. 6A

Temporal change of score based on facial image
(change in facial expression)

| Frame | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Calmness | 60 | 50 | 56 | 22 | 18 | 10 | 10 | 11 | 15 | 17 | 18 | 0 | 5 | 7 | 3 |
| Anger | 10 | 20 | 23 | 55 | 60 | 80 | 82 | 75 | 55 | 28 | 22 | 20 | 10 | 13 | 12 |
| Sadness | 10 | 20 | 11 | 12 | 12 | 5 | 5 | 10 | 25 | 55 | 60 | 80 | 83 | 75 | 80 |
| Joy | 20 | 10 | 10 | 11 | 10 | 5 | 3 | 4 | 5 | 0 | 0 | 0 | 2 | 5 | 5 |

FIG. 6B

Temporal change of score based on temperature
(change in temperature)

| Frame | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Calmness | 60 | 59 | 61 | 52 | 50 | 25 | 15 | 9 | 5 | 17 | 18 | 12 | 23 | 25 | 7 |
| Anger | 5 | 10 | 10 | 20 | 30 | 50 | 65 | 80 | 75 | 55 | 50 | 20 | 10 | 5 | 10 |
| Sadness | 10 | 8 | 9 | 8 | 10 | 10 | 10 | 6 | 15 | 18 | 23 | 55 | 62 | 65 | 78 |
| Joy | 25 | 23 | 20 | 20 | 10 | 15 | 10 | 5 | 5 | 10 | 9 | 13 | 5 | 5 | 5 |

FIG. 6C

Temporal change of determined emotion

| Frame | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Calmness | | | | | | | | | | | | | | | |
| Anger | | | | | | | | | | | | | | | |
| Sadness | | | | | | | | | | | | | | | |
| Joy | | | | | | | | | | | | | | | |

FIG. 10A Temporal change of score based on facial image (change in facial expression)
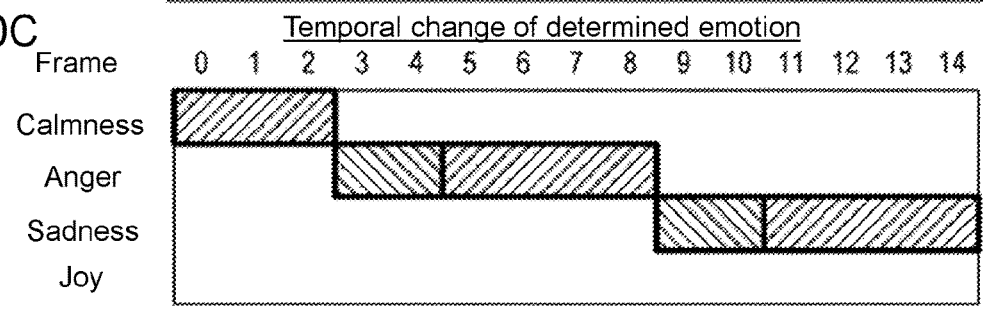
FIG. 10B Temporal change of score based on temperature (change in temperature)
FIG. 10C Temporal change of determined emotion
FIG. 11
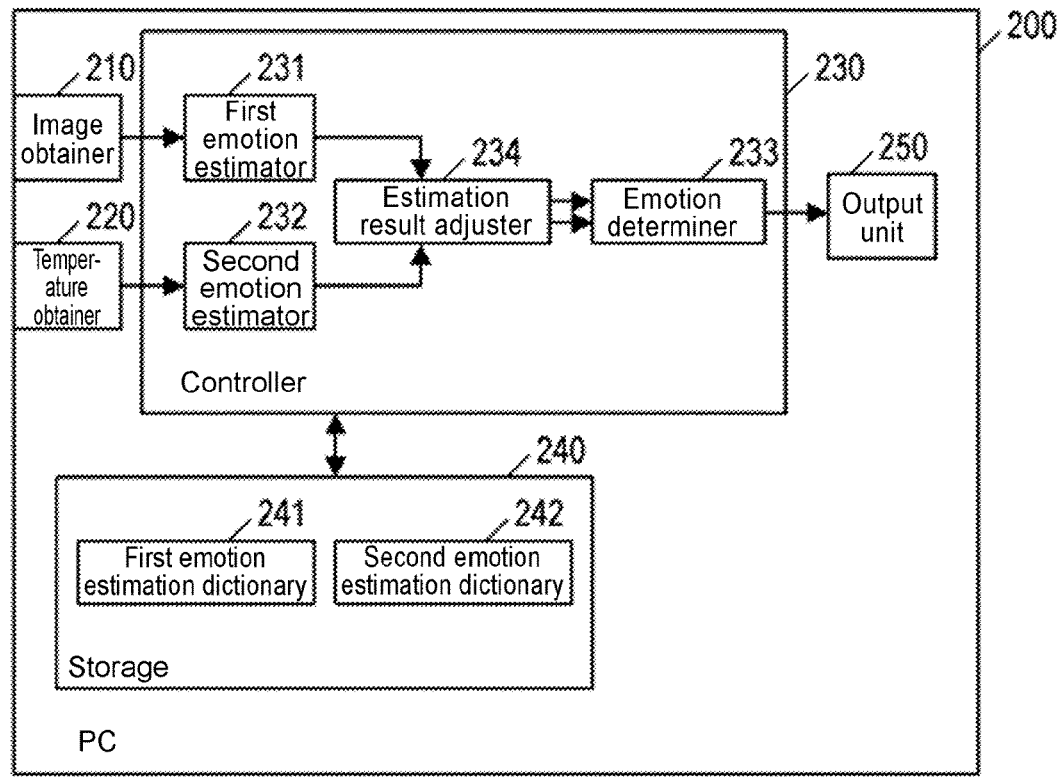

FIG. 12A

Temporal change of score based on facial image
(change in facial expression) (before change)

| Frame | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Calmness | 60 | 50 | 56 | 22 | 18 | 10 | 10 | 11 | 15 | 17 | 18 | 0 | 5 | 7 | 3 |
| Anger | 10 | 20 | 23 | 55 | 60 | 80 | 82 | 75 | 55 | 28 | 22 | 20 | 10 | 13 | 12 |
| Sadness | 10 | 20 | 11 | 12 | 12 | 5 | 5 | 10 | 25 | 55 | 60 | 80 | 83 | 75 | 80 |
| Joy | 20 | 10 | 10 | 11 | 10 | 5 | 3 | 4 | 5 | 0 | 0 | 0 | 2 | 5 | 5 |

FIG. 12B

Temporal change of score variance value for preceding three frames

| Frame | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Calmness | | | 16.9 | | | | | | | | | | | | |
| Anger | | | | 251 | 269 | 117 | 98.7 | 8.67 | 131 | | | | | | |
| Sadness | | | | | | | | | | 350 | 239 | 117 | 104 | 10.9 | 10.9 |
| Joy | | | | | | | | | | | | | | | |

FIG. 12C

Temporal change of score based on facial image
(change in facial expression) (after change)

| Frame | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Calmness | 56 | 56 | 56 | | | | | | | | | | | | |
| Anger | | | | 75 | 75 | 75 | 75 | 75 | | | | | | | |
| Sadness | | | | | | | | | 75 | 75 | 75 | 75 | 75 | 75 | 80 |
| Joy | | | | | | | | | | | | | | | |

FIG. 13A

Score calculated by first emotion estimator 231

| Frame | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Calmness | 60 | 50 | 56 | 22 | 18 | 10 | 10 | 11 | 15 | 17 | 18 | 0 | 5 | 7 | 3 |
| Anger | 10 | 20 | 23 | 55 | 60 | 80 | 82 | 75 | 55 | 28 | 22 | 20 | 10 | 13 | 12 |
| Sadness | 10 | 20 | 11 | 12 | 12 | 5 | 5 | 10 | 25 | 55 | 60 | 80 | 83 | 75 | 80 |
| Joy | 20 | 10 | 10 | 11 | 10 | 5 | 3 | 4 | 5 | 0 | 0 | 0 | 2 | 5 | 5 |

FIG. 13B

Score used in emotion determiner 233

| Frame | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Calmness | 60 | 60 | 60 | 22 | 22 | 22 | 10 | 10 | 10 | 17 | 17 | 17 | 5 | 5 | 5 |
| Anger | 10 | 10 | 10 | 55 | 55 | 55 | 82 | 82 | 82 | 28 | 28 | 28 | 10 | 10 | 10 |
| Sadness | 10 | 10 | 10 | 12 | 12 | 12 | 5 | 5 | 5 | 55 | 55 | 55 | 83 | 83 | 83 |
| Joy | 20 | 20 | 20 | 11 | 11 | 11 | 3 | 3 | 3 | 0 | 0 | 0 | 2 | 2 | 2 |

EMOTION DETERMINATION DEVICE AND EMOTION DETERMINATION METHOD

TECHNICAL FIELD

The present invention relates to a technique for determining the emotion of a user, such as calmness, anger, sadness, and joy.

BACKGROUND ART

A technique has been developed for determining the emotion of a user for, for example, intended control. A correct determination of user emotions allows, for example, control of the operation (e.g., speech) of a communication robot for intended communication with the user.

Techniques for determining emotions are described in, for example, Patent Literatures 1 to 3. Patent Literatures 1 to 3 describe techniques for determining emotions based on various sets of biometric data, such as brain waves and heartbeats measured with wearable devices.

CITATION LIST

Patent Literature

Patent Literature 1: Japanese Unexamined Patent Application Publication No. 2014-178970
Patent Literature 2: Japanese Unexamined Patent Application Publication No. 2017-144222
Patent Literature 3: Japanese Unexamined Patent Application Publication No.

SUMMARY OF INVENTION

Technical Problem

However, with the known techniques described in Patent Literatures 1 to 3, the user wears a wearable device and thus can have low usability. Such techniques also use numerous sets of biometric data, and involve a high processing load and a lengthy time for emotion determination.

In response to the above issue, one or more aspects of the present invention are directed to a technique for determining emotions with high accuracy using a simple structure with high usability.

Solution to Problem

The technique according to one or more aspects of the present invention has the structure described below.

An emotion determination device according to a first aspect of the present invention includes a first estimator that estimates an emotion of a user based on a change in a facial expression of the user detected from a face image of the user, a second estimator that estimates the emotion of the user based on a change in a temperature of the user detected contactlessly from the user, and a determiner that determines the emotion of the user based on an estimation result obtained by the first estimator and an estimation result obtained by the second estimator. The face image is, for example, an image obtained by capturing an image of a face with an image sensor (camera) or a portion of an image captured with an image sensor including a face. The temperature is detected contactlessly with, for example, a thermal sensor.

In the structure described above, the emotion can be determined with high accuracy using the simple structure based on the results of the emotion estimation using the face image and the temperature, without using numerous sets of biometric data. Further, both the face image and the temperature (detection value) are obtained contactlessly with high usability and without the user wearing any wearable device. Determining the emotion with high accuracy based on the facial image alone is difficult due to individual differences in facial expression changes and in the correspondence between the emotion and the facial expression. Determining the emotion with high accuracy based on the temperature alone is also difficult due to the temperature of the user that varies greatly depending on the environment (season and location such as indoors or outdoors) and clothing. The structure described above estimates the emotion by combining the result of the emotion determination (emotion estimation) using the face image with the result of the emotion determination using the temperature and achieves higher accuracy than the emotion determination using one of the face image or the temperature.

Each of the first estimator and the second estimator may calculate a score indicating a likelihood of the user holding an emotion of a plurality of emotions. The determiner may determine the emotion of the user based on a score for each of the plurality of emotions calculated by the first estimator and a score for each of the plurality of emotions calculated by the second estimator. The scores are normalized by the same criteria and thus are in the same range for the emotion estimation using the face image and the emotion estimation using the temperature. For example, the maximum score is commonly a predetermined value of, for example, 100, in the emotion estimation using the face image and the emotion estimation using the temperature. The multiple emotions include calmness, anger, sadness, and joy.

For example, the determiner may determine, as the emotion of the user, an emotion with a greatest score calculated by the first estimator matching an emotion with a greatest score calculated by the second estimator. The determiner may determine, in response to the emotion with a greatest score calculated by the first estimator not matching the emotion with a greatest score calculated by the second estimator, the emotion of the user based on a score for each of the plurality of emotions calculated by the first estimator and a score for each of the plurality of emotions calculated by the second estimator.

More specifically, in response to the emotion with a greatest score calculated by the first estimator not matching the emotion with a greatest score calculated by the second estimator, the determiner may determine, as the emotion of the user, an emotion with a greater calculated score for the emotion with the greatest score calculated by the first estimator and the emotion with the greatest score calculated by the second estimator. This structure yields a more reliable emotion as the determination result.

In response to the emotion with a greatest score calculated by the first estimator not matching the emotion with a greatest score calculated by the second estimator, the determiner may determine, as the emotion of the user, an emotion with a greater sum of a score calculated by the first estimator and a score calculated by the second estimator of the emotion with the greatest score calculated by the first estimator and the emotion with the greatest score calculated by the second estimator. This structure also yields a more reliable emotion as the determination result.

In response to the emotion with a greatest score calculated by the first estimator not matching the emotion with a greatest score calculated by the second estimator, the determiner may determine, as the emotion of the user, an emotion with a greater score change amount of the emotion with the greatest score calculated by the first estimator and the emotion with the greatest score calculated by the second estimator. This allows emotional changes to be detected more quickly.

In response to the emotion with a greatest score calculated by the first estimator not matching the emotion with a greatest score calculated by the second estimator, the determiner may determine, as the emotion of the user, an emotion with a greater score variance value of the emotion with the greatest score calculated by the first estimator and the emotion with the greatest score calculated by the second estimator. This structure also yields a more reliable emotion as the determination result. The variance value herein can be referred to as the degree of score prominence.

The emotion determination device may further include an adjuster that detects a period with a variance value, for the period up to a predetermined time, of scores indicating a likelihood of the user holding an estimated emotion being less than a predetermined threshold value and adjusts an estimation result obtained by the first estimator and an estimation result obtained by the second estimator to replace an estimation result from a first period with the variance value less than the predetermined threshold value backward up to a period immediately after a second period with the variance value less than the predetermined threshold value with an estimation result in the first period. The determiner may determine the emotion of the user based on the adjusted estimation result obtained by the adjuster. In this manner, the emotional changes can be smoothed for detection of the tendency with high accuracy. This allows intended control with, for example, emotional changes being predicted. When, for example, the emotion of the user tends to change from anger to sadness, the behavior (e.g., speech) of the communication robot can be controlled to communicate with an angry user while expecting that the emotion of the user may change to sadness.

Each of the first estimator and the second estimator may estimate the emotion of the user in a first cycle. The determiner may use the estimation result obtained by the first estimator and the estimation result obtained by the second estimator updated in a second cycle longer than the first cycle. This can reduce the processing load for the emotion determination.

An emotion determination method according to a second aspect of the present invention includes estimating an emotion of a user based on a change in a facial expression of the user detected from a face image of the user, estimating the emotion of the user based on a change in temperature of the user detected contactlessly from the user, and determining the emotion of the user based on an estimation result in the estimating based on the change in the facial expression and an estimation result in the estimating based on the change in the temperature.

One or more aspects of the present invention may be directed to an emotion determination system including at least one of the components or functions described above. One or more aspects of the present invention may also be directed to an emotion determination method or a control method for an emotion determination system including at least part of the above processes, a program for causing a computer to implement the method, or a non-transitory computer-readable storage medium storing the program. The above structure and processes may be combined with one another unless any technical contradiction arises.

Advantageous Effects of Invention

The technique according to the above aspects of the present invention allows determination of the emotion with high accuracy using the simple structure with high usability.

BRIEF DESCRIPTION OF DRAWINGS

FIG. 3 is a flowchart of an example procedure according to a first embodiment.

FIGS. 6A to 6C are diagrams showing operation examples in the second embodiment.

FIGS. 10A to 10C are diagrams showing operation examples in the fourth embodiment.

FIG. 11 is a block diagram of a PC (emotion determination device) according to a fifth embodiment.

FIGS. 12A to 12C are diagrams showing operation examples in the fifth embodiment.

FIGS. 13A and 13B are diagrams showing operation examples in a sixth embodiment.

DESCRIPTION OF EMBODIMENTS

Example Use

An example use of the present invention will now be described. With known techniques for determining the emotion of the user, such as calmness, anger, sadness, and joy, the user wears a wearable device and thus can have low usability. Such techniques also use numerous sets of biometric data, and involve a high processing load and a lengthy time for emotion determination.

Figure 1:
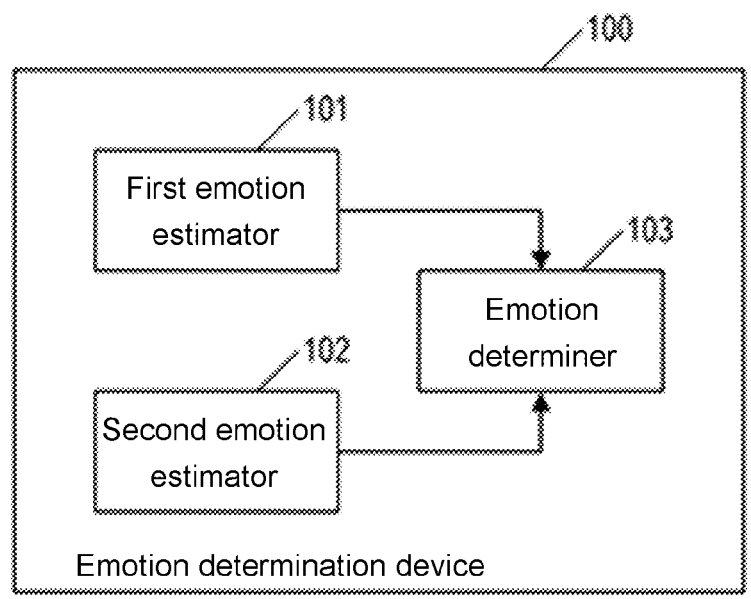
FIG. 1 is a block diagram of an emotion determination device according to one or more embodiments of the present invention.

FIG. 1 is a block diagram of an emotion determination device 100 according to one or more embodiments of the present invention. The emotion determination device 100 includes a first emotion estimator 101, a second emotion estimator 102, and an emotion determiner 103. The first emotion estimator 101 estimates the emotion of the user based on a change in the facial expression of the user detected in the face image of the user. The second emotion estimator 102 estimates the emotion of the user based on a change in the temperature of the user detected contactlessly from the user. The emotion determiner 103 determines the emotion of the user based on the estimation results obtained by the first emotion estimator 101 and the second emotion estimator 102. The first emotion estimator 101 is an example of a first estimator in an aspect of the present invention, the second emotion estimator 102 is an example of a second estimator in an aspect of the present invention, and the emotion determiner 103 is an example of a determiner in an aspect of the present invention. The face image is, for example, an image obtained by capturing an image of a face with an image sensor (camera) or a portion of an image captured with an image sensor including a face. The temperature is detected contactlessly with, for example, a thermal sensor.

The emotion determination device 100 with the above structure can determine the emotion with high accuracy using the simple structure based on the results of the emotion estimation using the face image and using the temperature without using numerous sets of biometric data. A correct determination of user emotions allows, for example, control of the operation (e.g., speech) of a communication robot for intended communication with the user. Further, both the face image and the temperature (detection value) are obtained contactlessly with high usability and without the user wearing any wearable device. Determining the emotion with high accuracy based on the facial image alone is difficult due to individual differences in facial expression changes and in the correspondence between the emotion and the facial expression. Determining the emotion with high accuracy based on the temperature alone is also difficult due to the temperature of the user that varies greatly depending on the environment (season and location such as indoors or outdoors) and clothing. In the structure described above, combining the result of the emotion determination (emotion estimation) using the face image with the result of the emotion determination using the temperature allows estimation of the emotion with higher accuracy than the emotion determination using one of the face image or the temperature.

First Embodiment

A first embodiment of the present invention will now be described.

(Structure)

Figure 2A:
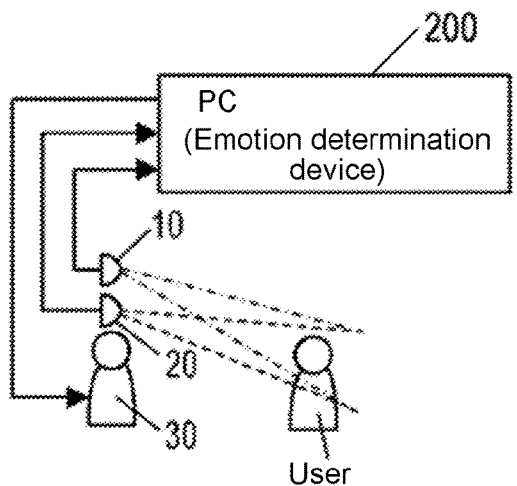
FIG. 2A is a schematic diagram of a communication system (emotion determination system) according to a first embodiment, showing an overall example structure.

FIG. 2A is a schematic diagram of a communication system (emotion determination system) according to the first embodiment, showing an overall example structure. The communication system according to the first embodiment includes a camera 10, a temperature measurement device 20, a personal computer (PC) 200 (emotion determination device), and a communication robot 30. The camera 10 and the PC 200 are connected to each other with a wire or wirelessly. Similarly, the temperature measurement device 20 and the PC 200 are connected to each other with a wire or wirelessly, and the PC 200 and the communication robot 30 are connected to each other with a wire or wirelessly.

The camera 10 captures an image using an image sensor incorporated in the camera 10 and outputs the captured image to the PC 200. In the first embodiment, the camera 10 outputs a face image obtained by capturing an image of the face of the user to the PC 200. The temperature measurement device 20 measures temperature using a thermal sensor incorporated in the temperature measurement device 20 and outputs the measurement result (temperature information) to the PC 200. In the first embodiment, the temperature measurement device 20 detects the temperature of the user (e.g., facial temperature) and outputs the temperature information indicating the detected temperature (detected value of the temperature) to the PC 200. The PC 200 determines the emotion of the user based on the facial image and the temperature of the user, and outputs the result of the emotion determination to the communication robot 30. The communication robot 30 communicates with the user based on the result of the determination of the emotion of the user.

The camera 10 may capture a larger area than the face area. In this case, for example, the camera 10 or the PC 200 may perform a process for obtaining a face image from an image captured with the camera 10 (detecting a face from a captured image). The temperature measurement device 20 may also detect a temperature distribution over a larger area than the user (face) area. In this case, for example, the temperature measurement device 20 or the PC 200 may perform a process for obtaining the temperature of the user from the detected temperature distribution. The use of the result of the determination of the emotion of the user is not limited and may not be for the control of the communication robot 30.

In the first embodiment, the camera 10, the temperature measurement device 20, the PC 200, and the communication robot 30 are separate devices, but are not limited to this structure. For example, at least two or more of the camera 10, the temperature measurement device 20, the PC 200, and the communication robot 30 may be included in one device. More specifically, the camera 10, the temperature measurement device 20, and the PC 200 may be sensors incorporated in the communication robot 30. The PC 200 may be at any location. For example, the PC 200 may or may not be located in the same room as the camera 10, the temperature measurement device 20, and the communication robot 30. The PC 200 may or may not be a cloud computer.

Figure 2B:
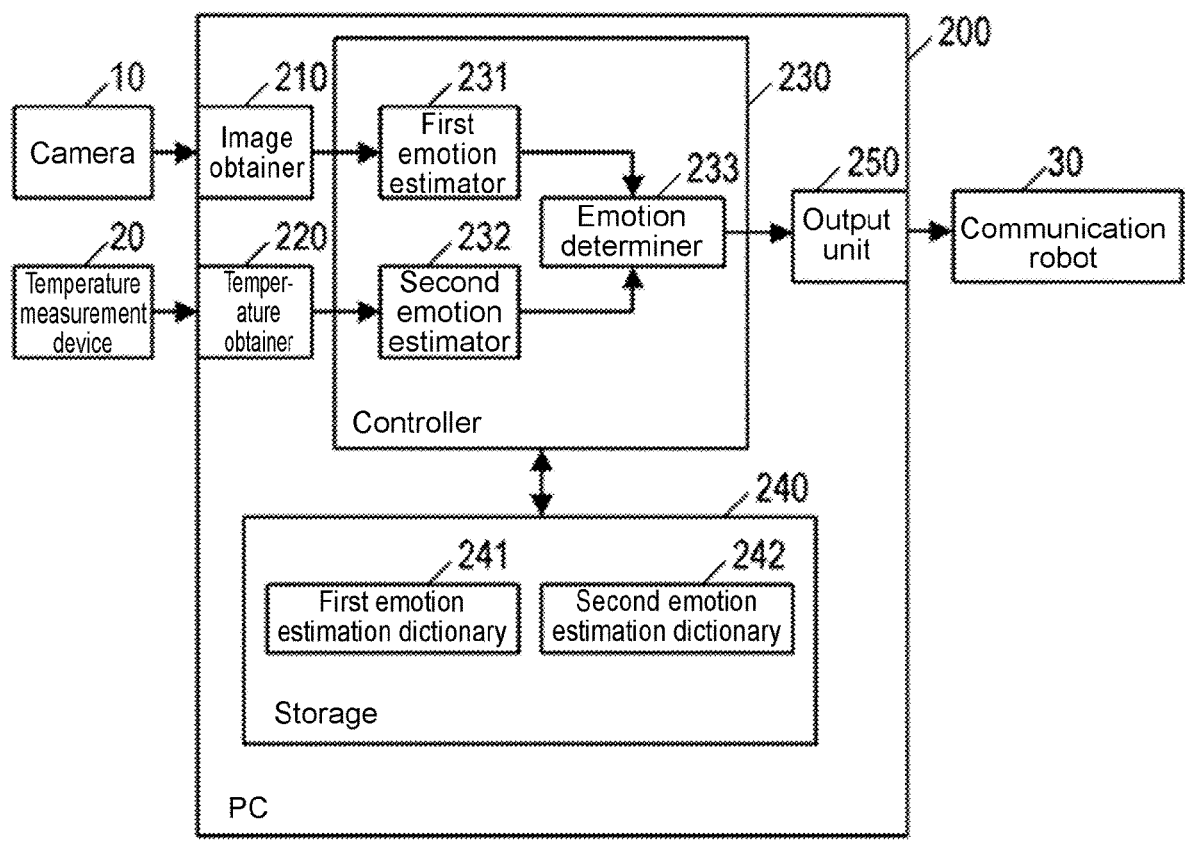
FIG. 2B is a block diagram of a personal computer (PC, or an emotion determination device) according to the first embodiment.

FIG. 2B is a block diagram of the PC 200. The PC 200 includes an image obtainer 210, a temperature obtainer 220, a controller 230, a storage 240, and an output unit 250.

The image obtainer 210 obtains a face image from the camera 10 and outputs the face image to the controller 230 (first emotion estimator 231). In the first embodiment, the camera 10 captures a video, and the image obtainer 210 performs a process for obtaining one frame of the video from the camera 10 and outputting the frame to the controller 230 sequentially. Although the cycle of face image obtainment by the image obtainer 210 is not limited, the image obtainer 210 obtains a face image (one frame of a video) synchronously with the image capturing with the camera 10 in the first embodiment. In other words, the image obtainer 210 performs the process for obtaining the face image from the camera 10 and outputting the face image to the controller 230 at the frame rate of the image capturing with the camera 10 (e.g., 30 fps). The camera 10 may capture still images sequentially. The image obtainer 210 may then perform a process for obtaining still images from the camera 10 and outputting the still images to the controller 230 sequentially.

The temperature obtainer 220 obtains the temperature information about the user from the temperature measurement device 20 and outputs the temperature information to the controller 230 (second emotion estimator 232). The cycle of the temperature measurement by the temperature measurement device 20 and the cycle of the temperature information obtainment by the temperature obtainer 220 are not limited. In the first embodiment, the temperature measurement device 20 measures the temperature synchronously with the image capturing with the camera 10, and the temperature obtainer 220 obtains the temperature information synchronously with the image capturing with the camera 10 (obtainment of the face image by the image obtainer 210). In other words, the temperature obtainer 220 performs the process for obtaining the temperature information from the temperature measurement device 20 and outputting the temperature information to the controller 230 at the frame rate of the image capturing with the camera 10.

The controller 230 includes, for example, a central processing unit (CPU), a random-access memory (RAM), and a read-only memory (ROM) to control each unit and perform various information processes. As described in detail later, in the first embodiment, the controller 230 determines the emotion of the user based on the face image obtained by the image obtainer 210 and the temperature information obtained by the temperature obtainer 220 and outputs the emotion determination result to the output unit 250.

The storage 240 stores a program executable by the controller 230 and various sets of data usable by the controller 230. For example, the storage 240 is an auxiliary storage device, such as a hard disk drive or a solid-state drive.

The output unit 250 outputs the determination result (determination result of the emotion) output by the controller 230 to the communication robot 30.

The storage 240 will now be described in more detail. The storage 240 includes a first emotion estimation dictionary 241 and a second emotion estimation dictionary 242. The first emotion estimation dictionary 241 stores the correspondence between the change in the facial expression and the emotion registered in advance. The second emotion estimation dictionary 242 stores the correspondence between the change in the temperature and the emotion registered in advance.

The controller 230 will now be described in more detail. The controller 230 includes the first emotion estimator 231, the second emotion estimator 232, and an emotion determiner 233.

The first emotion estimator 231 sequentially performs a process for detecting the facial expression of the user from the face image output by the image obtainer 210 (expression detection). The first emotion estimator 231 refers to the first emotion estimation dictionary 241 to estimate the emotion of the user from a change in the detected facial expression. The first emotion estimator 231 then outputs the emotion estimation result to the emotion determiner 233. The first emotion estimator 231 is an example of the first estimator in an aspect of the present invention.

Any algorithm may be used for the facial expression detection and the emotion estimation (both processing based on the face image) performed by the first emotion estimator 231. For example, the facial expression of the user may be detected through existing facial expression detection, or specifically with a detector (discriminator) that combines an image feature such as a histogram of oriented gradients (HoG) or a Haar-like feature and boosting. The facial expression may be detected using a trained model generated through existing machine learning, or specifically using a trained model generated by deep learning, examples of which include a region-based convolutional neural networks (R-CNN), Fast R-CNN, you only look once (YOLO), or a single shot multibox detector (SSD). Similarly, the emotion of the user may be estimated through existing emotion estimation or using a trained model generated by existing machine learning. More specifically, a trained model generated by deep learning (e.g., R-CNN, Fast R-CNN, YOLO, and SSD) may be used to estimate the emotion of the user.

The second emotion estimator 232 sequentially obtains the temperature information output by the temperature obtainer 220, refers to the second emotion estimation dictionary 242, and estimates the emotion of the user from the change in the obtained temperature information (change in the temperature of the user). The second emotion estimator 232 then outputs the emotion estimation result to the emotion determiner 233. The second emotion estimator 232 is an example of the second estimator in an aspect of the present invention.

Any algorithm may be used for emotion estimation (emotion estimation based on the temperature) performed by the second emotion estimator 232. For example, the emotion of the user may be estimated through existing emotion estimation or using a trained model generated by existing machine learning. More specifically, a trained model generated by deep learning (e.g., R-CNN, Fast R-CNN, YOLO, and SSD) may be used to estimate the emotion of the user.

The emotion determiner 233 determines the emotion of the user based on the estimation results obtained by the first emotion estimator 231 and the second emotion estimator 232 and outputs the emotion determination result to the output unit 250. The emotion determiner 233 is an example of the determiner in an aspect of the present invention.

In the first embodiment, each of the first emotion estimator 231 and the second emotion estimator 232 calculates a score indicating the likelihood of the user holding the emotion for each of the multiple emotions, and outputs the score for each emotion as the estimation result. The emotion determiner 233 then determines the emotion of the user based on the scores for each emotion calculated by the first emotion estimator 231 and of each calculated by the second emotion estimator 232.

The scores are herein normalized by the same criteria in the emotion estimation using the face image (emotion estimation performed by the first emotion estimator 231) and the emotion estimation using the temperature (emotion estimation performed by the second emotion estimator 232), and the range of the scores is common. For example, the maximum score is commonly a predetermined value of, for example, 100, in the emotion estimation using the face image and the emotion estimation using the temperature. In the first embodiment, the score for each emotion is calculated to cause the sum of the respective multiple scores corresponding to the multiple emotions to be 100 in each of the emotion estimation using the face image and the emotion estimation using the temperature. Although the number of multiple emotions and their types are not limited, four emotions of calmness, anger, sadness, and joy are used in the first embodiment.

When the emotion with the greatest score calculated by the first emotion estimator 231 matches the emotion with the greatest score calculated by the second emotion estimator 232, the user is highly likely to hold the emotion. The emotion determiner 233 thus determines the emotion with the greatest scores calculated by the first emotion estimator 231 and the second emotion estimator 232 as the emotion of the user.

The emotion with the greatest score calculated by the first emotion estimator 231 may not match the emotion with the greatest score calculated by the second emotion estimator 232. In such a case, the emotion determiner 233 determines the emotion of the user based on the score for each emotion calculated by the first emotion estimator 231 and the score for each emotion calculated by the second emotion estimator 232. More specifically, the emotion determiner 233 determines the emotion with the greater calculated score for the emotion with the greatest score calculated by the first emotion estimator 231 and the emotion with the greatest score calculated by the second emotion estimator 232 as the emotion of the user. A greater score is expected to indicate a higher reliability (a higher likelihood of the user holding the corresponding emotion), thus yielding a more reliable emotion as the determination result.

(Operation)

FIG. 3 is a flowchart of an example procedure according to the first embodiment. The PC 200 repeats the procedure in FIG. 3. Although the repetition cycle of the procedure in FIG. 3 is not limited, the procedure in FIG. 3 is repeated at the frame rate of the image capturing with the camera 10 (e.g., 30 fps).

First, the image obtainer 210 obtains the face image of the user from the camera 10 (step S301). The first emotion estimator 231 then detects the facial expression of the user from the face image obtained in step S301, and calculates each score for calmness, anger, sadness, and joy based on a change in the detected facial expression (change in the facial expression from the past to the present) (step S302).

The temperature obtainer 220 then obtains the temperature information about the user (temperature of the user) from the temperature measurement device 20 (step S303). The second emotion estimator 232 then calculates each score for calmness, anger, sadness, and joy based on a change in the temperature of the user (change in the temperature from the past to the present) (step S304).

The emotion determiner 233 then determines whether an emotion E1 with the greatest score calculated by the first emotion estimator 231 matches an emotion E2 with the greatest score calculated by the second emotion estimator 232 (step S305). The emotion E1 has the greatest score of the four scores (respectively corresponding to calmness, anger, sadness, and joy) calculated in step S302 based on the change in the facial expression. The emotion E2 has the greatest score of the four scores (respectively corresponding to calmness, anger, sadness, and joy) calculated in step S304 based on the change in the temperature. Once the emotion E1 matches the emotion E2 (Yes in step S305), the processing advances to step S306, and when the emotion E1 does not match the emotion E2 (No in step S305), the processing advances to step S307.

In step S306, the emotion determiner 233 determines the emotion E1=the emotion E2 as the emotion Eresult (final determination result) of the user. The PC 200 then ends the procedure in FIG. 3.

In step S307, the emotion determiner 233 determines whether the score for the emotion E1 (score based on the change in the facial expression) matches the score for the emotion E2 (score based on the change in the temperature). When the score for the emotion E1 does not match the score for the emotion E2 (No in step S307), the processing advances to step S308. Once the score for the emotion E1 matches the score for the emotion E2 (Yes in step S307), the PC 200 ends the procedure in FIG. 3. The same emotion as the previous emotion is then used as the emotion Eresult of the user.

In step S308, the emotion determiner 233 determines whether the score for the emotion E1 is greater than the score for the emotion E2. When the score for the emotion E1 is greater than the score for the emotion E2 (Yes in step S308), the processing advances to step S309. When the score for the emotion E1 is less than the score for the emotion E2 (No in step S308), the processing advances to step S310.

In step S309, the emotion determiner 233 determines the emotion E1 (emotion estimated based on the change in the facial expression) as the emotion Eresult of the user. The PC 200 then ends the procedure in FIG. 3.

In step S310, the emotion determiner 233 determines the emotion E2 (emotion estimated based on the change in the temperature) as the emotion Eresult of the user. The PC 200 then ends the procedure in FIG. 3.

(Specific Operation Example)

Figures 4A, 4B, 4C:
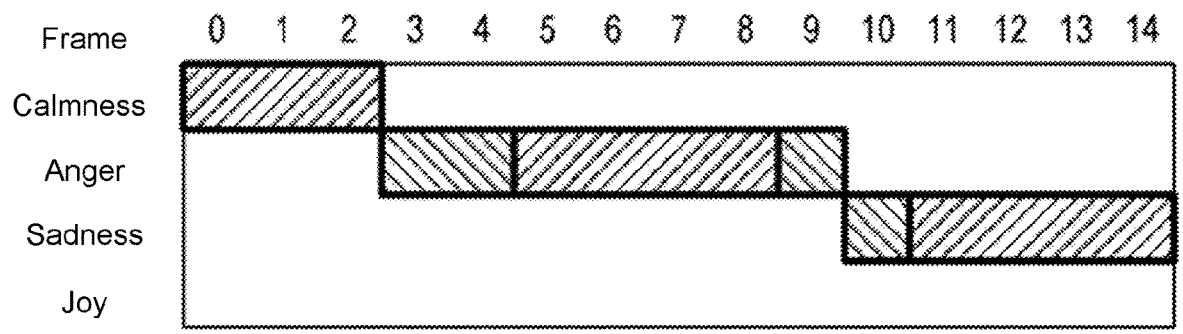
FIGS. 4A to 4C are diagrams showing operation examples in the first embodiment.

FIGS. 4A to 4C show operation examples in the first embodiment. FIG. 4A shows an example temporal change of the score for each emotion (score based on the change in the facial expression) calculated by the first emotion estimator 231. In FIG. 4A, the emotion E1 (emotion estimated based on the change in the facial expression) is shown in bold frames. FIG. 4B shows an example temporal change of the score for each emotion (score based on the change in the temperature) calculated by the second emotion estimator 232. In FIG. 4B, the emotion E2 (emotion estimated based on the change in the temperature) is shown in bold frames. FIG. 4C shows an example temporal change of the emotion (emotion Eresult) determined by the emotion determiner 233.

In the examples in FIGS. 4A to 4C, both the emotions E1 and E2 are calmness for the period from frame 0 to frame 2, and calmness is thus determined as the emotion Eresult. For frame 3, the emotion E1 is anger, and the emotion E2 is calmness. The emotions E1 and E2 are different. The score for the emotion E1 (anger) is 55. The score for the emotion E2 (calmness) is 52. Based on the score (55) for the emotion E1 (anger) greater than the score (52) for emotion E2 (calmness), anger is determined as the emotion Eresult. Similarly in the other frames, the emotion Eresult is determined based on, for example, the match or mismatch between the score for the emotion E1 and the score for the emotion E2, and on the relationship between the score for the emotion E1 and the score for the emotion E2.

(Overview)

In the first embodiment as described above, the emotion can be determined with high accuracy using the simple structure based on the result of the emotion estimation using the face image and the temperature, without using numerous sets of biometric data. Further, both the face image and the temperature (detection value) are obtained contactlessly with high usability and without the user wearing any wearable device. In addition, determining the emotion with the greater calculated score for the emotion estimated based on the face image and the emotion estimated based on the temperature as the emotion of the user can yield a more reliable emotion as the determination result.

Second Embodiment

A second embodiment of the present invention will now be described.

(Structure)

The structures of the communication system and the PC 200 according to the second embodiment are substantially the same as in the first embodiment. In the second embodiment, the processing performed by the emotion determiner 233 differs from the processing in the first embodiment for the emotion with the greatest score calculated by the first emotion estimator 231 not matching the emotion with the greatest score calculated by the second emotion estimator 232. In the second embodiment, the emotion determiner 233 determines, as the emotion of the user, the emotion with the greater sum of a score calculated by the first estimator 231 and a score calculated by the second estimator 232 of the emotion with the greatest score calculated by the first estimator 231 and the emotion with the greatest score calculated by the second estimator 232. This structure also yields a more reliable emotion as the determination result.

(Operation)

Figure 5:
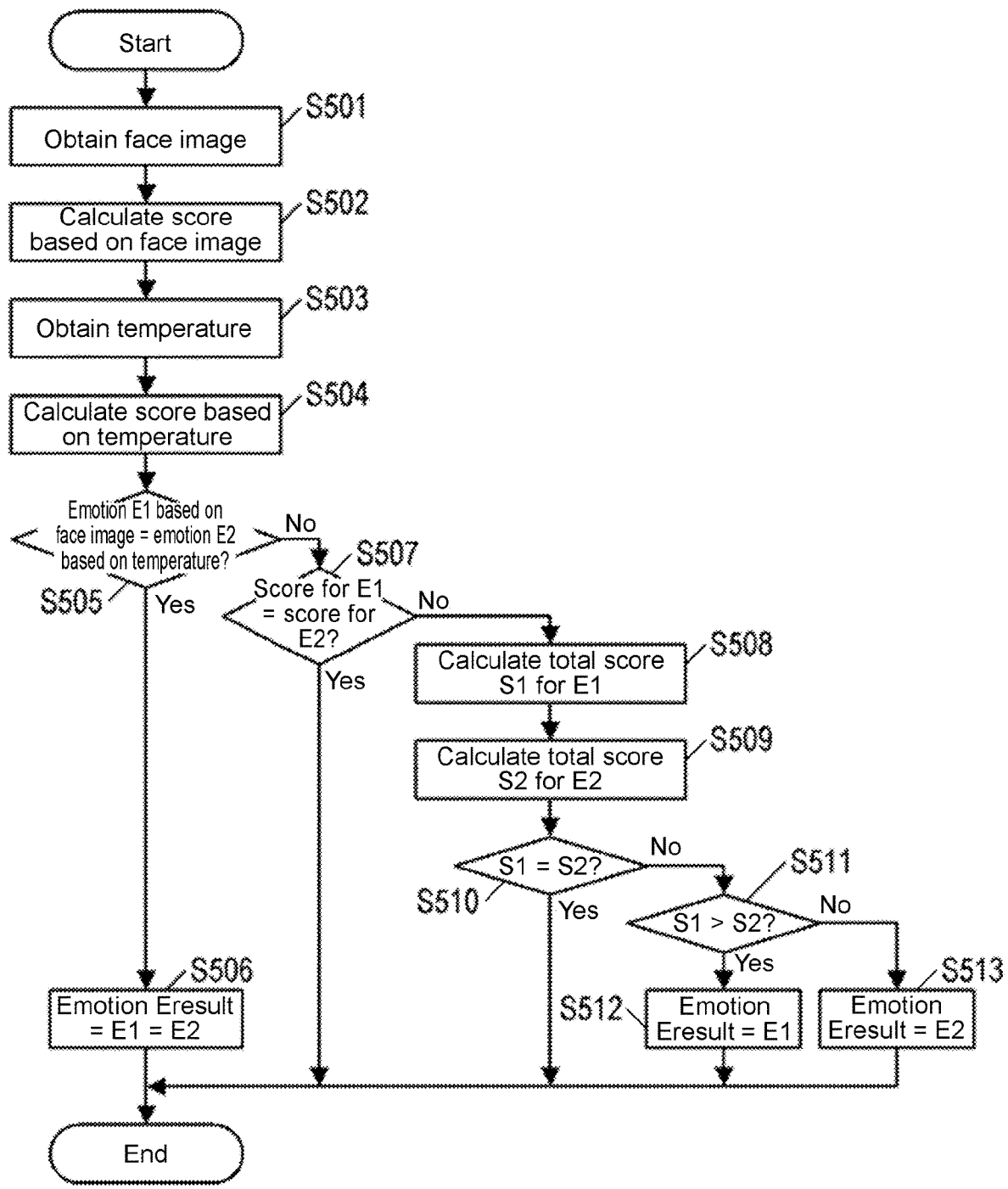
FIG. 5 is a flowchart of an example procedure according to a second embodiment.

FIG. 5 is a flowchart of an example procedure according to the second embodiment. The PC 200 repeats the procedure in FIG. 5. Although the repetition cycle of the procedure in FIG. 5 is not limited, the procedure in FIG. 5 is repeated at the frame rate of the image capturing with the camera 10 (e.g., 30 fps).

The processing in steps S501 to S507 is the same as the processing in steps S301 to S307 in the first embodiment. When the score for the emotion E1 (score based on the change in the facial expression) does not match the score for the emotion E2 (score based on the change in the temperature) (No in step S507), the processing advances to step S508.

In step S508, the emotion determiner 233 calculates a total score S1 corresponding to the emotion E1. The total score S1 is calculated by adding the score for the emotion E1 (score calculated by the first emotion estimator 231, or specifically, the score based on the change in the facial expression) and the score calculated by the second emotion estimator 232 (score based on the change in the temperature) for the same emotion as the emotion E1.

In step S509, the emotion determiner 233 calculates a total score S2 corresponding to the emotion E2. The total score S2 is calculated by adding the score for the emotion E2 (score calculated by the second emotion estimator 232, or specifically, the score based on the change in the temperature) and the score calculated by the first emotion estimator 231 (score based on the change in the facial expression) for the same emotion as the emotion E2.

In step S510, the emotion determiner 233 determines whether the total score S1 calculated in step S508 matches the total score S2 calculated in step S509. When the total score S1 does not match the total score S2 (No in step S510), the processing advances to step S511. Once the total score S1 matches the total score S2 (Yes in step S510), the PC 200 ends the procedure in FIG. 5. The same emotion as the previous emotion is then used as the emotion Eresult of the user.

In step S511, the emotion determiner 233 determines whether the total score S1 calculated in step S508 is greater than the total score S2 calculated in step S509. When the total score S1 is greater than the total score S2 (Yes in step S511), the processing advances to step S512. When the total score S1 is less than the total score S2 (No in step S511), the processing advances to step S513.

In step S512, the emotion determiner 233 determines the emotion E1 corresponding to the total score S1 as the emotion Eresult of the user. The PC 200 then ends the procedure in FIG. 5.

In step S513, the emotion determiner 233 determines the emotion E2 corresponding to the total score S2 as the emotion Eresult of the user. The PC 200 then ends the procedure in FIG. 5.

(Specific Operation Example)

FIGS. 6A to 6C show operation examples in the second embodiment. FIG. 6A shows an example temporal change of the score for each emotion (score based on the change in the facial expression) calculated by the first emotion estimator 231. In FIG. 6A, the emotion E1 (emotion estimated based on the change in the facial expression) is shown in bold frames. FIG. 6B shows an example temporal change of the score for each emotion (score based on the change in the temperature) calculated by the second emotion estimator 232. In FIG. 6B, the emotion E2 (emotion estimated based on the change in the temperature) is shown in bold frames. FIG. 6C shows an example temporal change of the emotion (emotion Eresult) determined by the emotion determiner 233.

In the examples in FIGS. 6A to 6C, both the emotions E1 and E2 are calmness for the period from frame 0 to frame 2, and calmness is thus determined as the emotion Eresult. For frame 3, the emotion E1 is anger, and the emotion E2 is calmness. The emotions E1 and E2 are different. For the emotion E1 (anger), the sum (total score S1) of the score (55) calculated by the first emotion estimator 231 and the score (20) calculated by the second emotion estimator 232 is 75. For the emotion E2 (calmness), the sum (total score S2) of the score (22) calculated by the first emotion estimator 231 and the score (52) calculated by the second emotion estimator 232 is 74. With the total score S1 (75) corresponding to the emotion E1 (anger) greater than the total score S2 (74) corresponding to the emotion E2 (calmness), anger is determined as the emotion Eresult. Similarly in the other frames, the emotion Eresult is determined based on, for example, the match or mismatch between the score for the emotion E1 and the score for the emotion E2, and on the relationship between the total score S1 and the total score S2.

(Overview)

In the second embodiment as described above, the highly accurate emotion determination can be achieved using the simple structure with high usability, as in the first embodiment. In addition, determining the emotion with the greater sum of the score based on the face image and the score based on the temperature of the emotion estimated based on the face image and the emotion estimated based on the temperature as the emotion of the user can yield a more reliable emotion as the determination result.

Third Embodiment

A third embodiment of the present invention will now be described.

(Structure)

The structures of the communication system and the PC 200 according to the third embodiment are substantially the same as in the first embodiment. In the third embodiment, the processing performed by the emotion determiner 233 differs from the processing in the first embodiment for the emotion with the greatest score calculated by the first emotion estimator 231 not matching the emotion with the greatest score calculated by the second emotion estimator 232. In the third embodiment, the emotion determiner 233 determines the emotion with the greater score change amount from the previous score for those emotions as the emotion of the user. In this manner, the emotional change can be detected more quickly.

(Operation)

Figure 7:
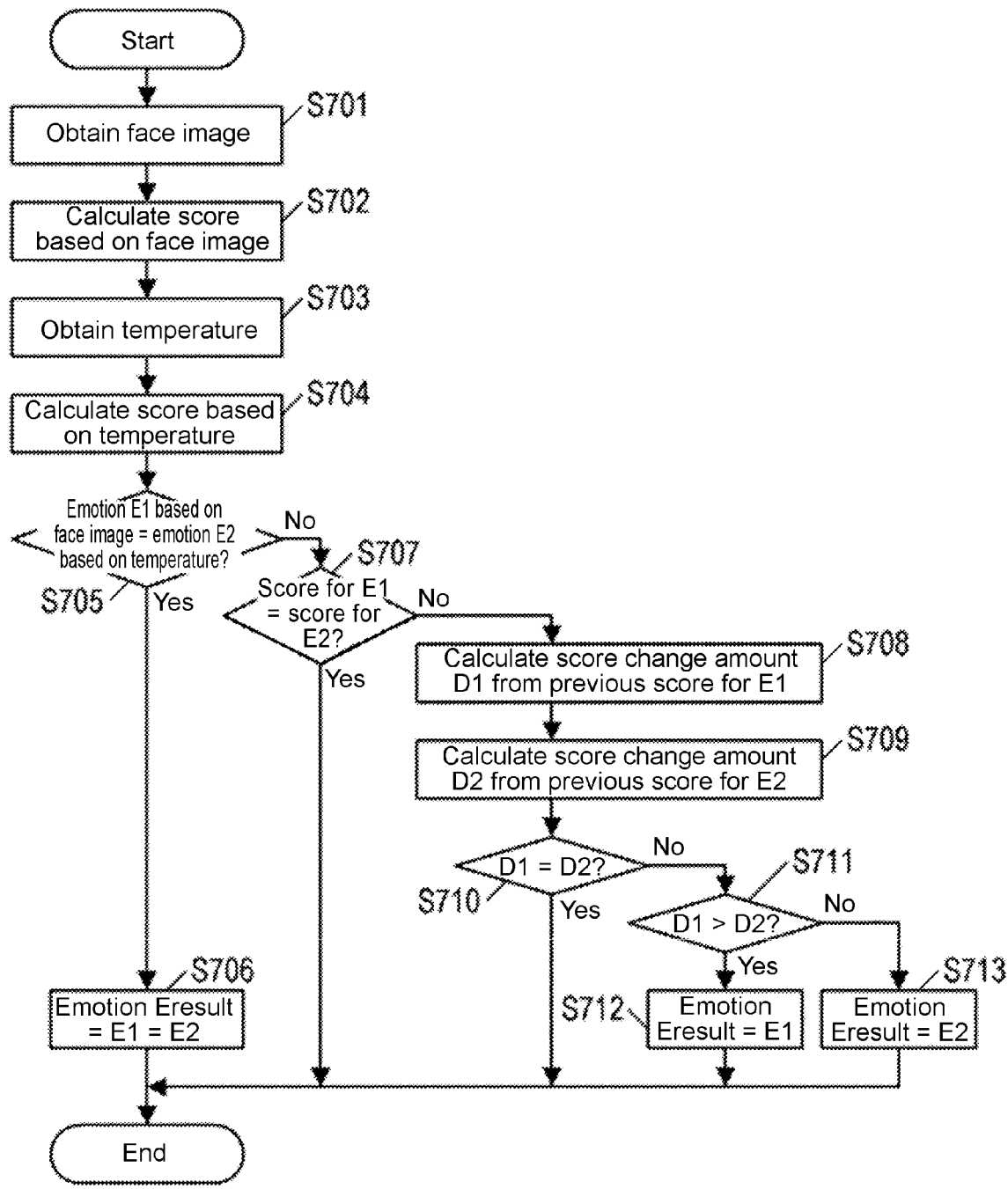
FIG. 7 is a flowchart of an example procedure according to a third embodiment.

FIG. 7 is a flowchart of an example procedure according to the third embodiment. The PC 200 repeats the procedure in FIG. 7. Although the repetition cycle of the procedure in FIG. 7 is not limited, the procedure in FIG. 7 is repeated at the frame rate of the image capturing with the camera 10 (e.g., 30 fps).

The processing in steps S701 to S707 is the same as the processing in steps S301 to S307 in the first embodiment. When the score for the emotion E1 (score based on the change in the facial expression) does not match the score for the emotion E2 (score based on the change in the temperature) (No in step S707), the processing advances to step S708.

In step S708, the emotion determiner 233 calculates a change amount D1 from the previous score for the emotion E1 (score based on the expression change) to the present score for the emotion E1 (score based on the expression change). The change amount D1 is a difference value obtained by subtracting the previous score for the emotion E1 from the present score for the emotion E1.

In step S709, the emotion determiner 233 calculates a change amount D2 from the previous score for the emotion E2 (score based on the change in the temperature) to the present score for the emotion E2 (score based on the change in the temperature). The change amount D2 is a difference value obtained by subtracting the previous score for the emotion E2 from the present score for the emotion E2.

In step S710, the emotion determiner 233 determines whether the change amount D1 calculated in step S708 matches the change amount D2 calculated in step S709. When the change amount D1 does not match the change amount D2 (No in step S710), the processing advances to step S711. Once the change amount D1 matches the change amount D2 (Yes in step S710), the PC 200 ends the procedure in FIG. 7. The same emotion as the previous emotion is then used as the emotion Eresult of the user.

In step S711, the emotion determiner 233 determines whether the change amount D1 calculated in step S708 is greater than the change amount D2 calculated in step S709. When the change amount D1 is greater than the change amount D2 (Yes in step S711), the processing advances to step S712. When the change amount D1 is less than the change amount D2 (No in step S711), the processing advances to step S713.

In step S712, the emotion determiner 233 determines the emotion E1 corresponding to the change amount D1 as the emotion Eresult of the user. The PC 200 then ends the procedure in FIG. 7.

In step S713, the emotion determiner 233 determines the emotion E2 corresponding to the change amount D2 as the emotion Eresult of the user. The PC 200 then ends the procedure in FIG. 7.

(Specific Operation Example)

Figure 8:
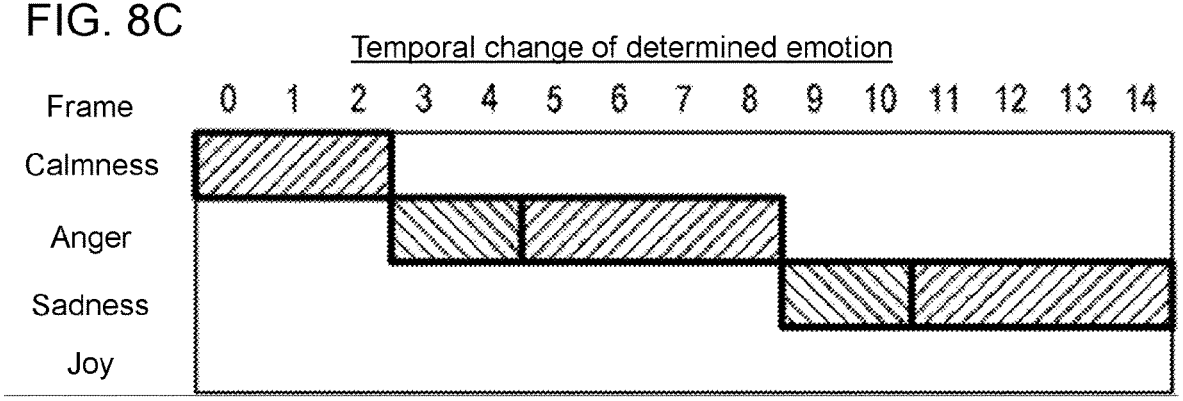
FIGS. 8A to 8C are diagrams showing operation examples in the third embodiment.

FIGS. 8A to 8C show operation examples in the third embodiment. FIG. 8A shows an example temporal change of the score for each emotion (score based on the change in the facial expression) calculated by the first emotion estimator 231. In FIG. 8A, the emotion E1 (emotion estimated based on the change in the facial expression) is shown in bold frames. FIG. 8B shows an example temporal change of the score for each emotion (score based on the change in the temperature) calculated by the second emotion estimator 232. In FIG. 8B, the emotion E2 (emotion estimated based on the change in the temperature) is shown in bold frames. FIG. 8C shows an example temporal change of the emotion (emotion Eresult) determined by the emotion determiner 233.

In the examples in FIGS. 8A to 8C, both the emotions E1 and E2 are calmness for the period from frame 0 to frame 2, and calmness is thus determined as the emotion Eresult. For frame 3, the emotion E1 is anger, and the emotion E2 is calmness. The emotions E1 and E2 are different. For the emotion E1 (anger), the change amount D1 from the previous score calculated by the first emotion estimator 231 (23, or specifically, the score for frame 2) to the present score calculated by the first emotion estimator 231 (55, or specifically, the score for frame 3) is 32 (=55−23). For the emotion E2 (calmness), the change amount D2 from the previous score calculated by the second emotion estimator 232 (61, or specifically, the score for frame 2) to the present score calculated by the second emotion estimator 232 (52, or specifically, the score for frame 3) is −9 (=52−61). With the change amount D1 (32) corresponding to the emotion E1 (anger) is greater than the change amount D2 (−9) corresponding to the emotion E2 (calmness), anger is determined as the emotion Eresult. Similarly in other frames, the emotion Eresult is determined based on, for example, the match or mismatch between the score for the emotion E1 and the score for the emotion E2, and on the relationship between the change amount D1 and the change amount D2.

(Overview)

In the third embodiment as described above, the highly accurate emotion determination can be achieved using the simple structure with high usability, as in the first embodiment. In addition, determining the emotion with the greater score change amount from the previous score for the emotion estimated based on the face image and the emotion estimated based on the temperature as the emotion of the user can capture the emotional change more quickly.

Fourth Embodiment

A fourth embodiment of the present invention will now be described.

(Structure)

The structures of the communication system and the PC 200 according to the fourth embodiment are substantially the same as in the first embodiment. In the fourth embodiment, the processing performed by the emotion determiner 233 differs from the processing in the first embodiment for the emotion with the greatest score calculated by the first emotion estimator 231 not matching the emotion with the greatest score calculated by the second emotion estimator 232. In the fourth embodiment, the emotion determiner 233 determines the emotion with the greater score variance value among the multiple emotions of those emotions as the emotion of the user. The variance value herein can be referred to as the degree of score prominence. A greater score variance value among multiple emotions, or in other words, a more prominent greatest score indicates a higher reliability (likelihood of the user holding the corresponding emotion), and thus a more reliable emotion as the determination result. A variance value V of n scores Xi (i is an integer from 1 to n inclusive) can be calculated using, for example, Formula 1 described below. In Formula 1, Xave is the average of the n scores Xi.

Formula 1

$$V = \frac{1}{n}\sum_{i=1}^{n}(Xi - Xave)^2 \quad (1)$$

(Operation)

Figure 9:
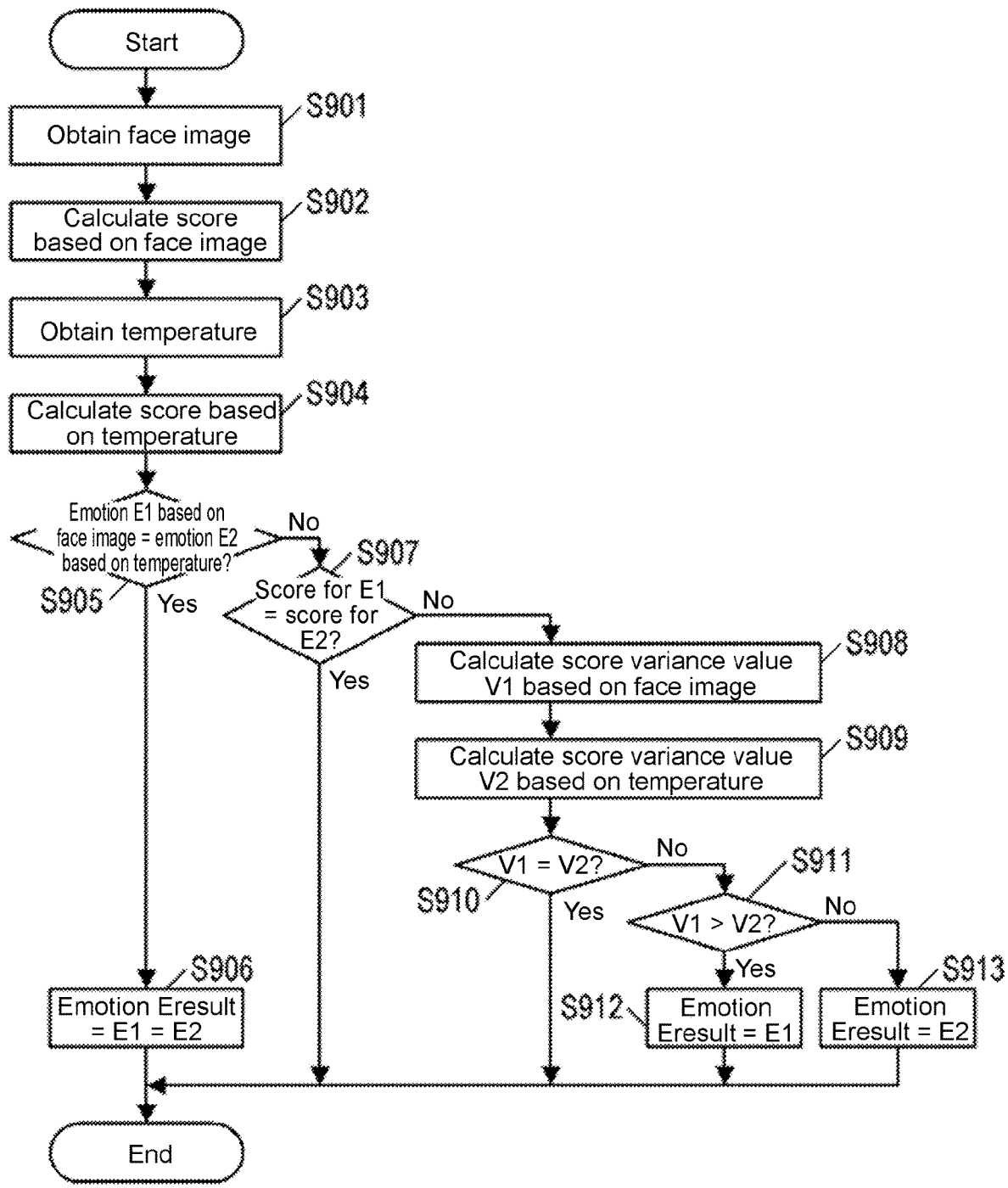
FIG. 9 is a flowchart of an example procedure according to a fourth embodiment.

FIG. 9 is a flowchart of an example procedure according to the fourth embodiment. The PC 200 repeats the procedure in FIG. 9. Although the repetition cycle of the procedure in FIG. 9 is not limited, the procedure in FIG. 9 is repeated at the frame rate of the image capturing with the camera 10 (e.g., 30 fps).

The processing in steps S901 to S907 is the same as the processing in steps S301 to S307 in the first embodiment. When the score for the emotion E1 (score based on the change in the facial expression) does not match the score for the emotion E2 (score based on the change in the temperature) (No in step S907), the processing advances to step S908.

In step S908, the emotion determiner 233 calculates each variance value of multiple scores (multiple scores based on the change in the facial expression) calculated by the first emotion estimator 231 for multiple emotions (calmness, anger, sadness, and joy) as a variance value V1 corresponding to the emotion E1.

In step S909, the emotion determiner 233 calculates each variance value of multiple scores (multiple scores based on the change in the temperature) calculated by the second emotion estimator 232 for multiple emotions (calmness, anger, sadness, and joy) as a variance value V2 corresponding to the emotion E2.

In step S910, the emotion determiner 233 determines whether the variance value V1 calculated in step S908 matches the variance value V2 calculated in step S909. When the variance value V1 does not match the variance value V2 (No in step S910), the processing advances to step S911. Once the variance value V1 matches the variance value V2 (Yes in step S910), the PC 200 ends the procedure in FIG. 9. The same emotion as the previous emotion is then used as the emotion Eresult of the user.

In step S911, the emotion determiner 233 determines whether the variance value V1 calculated in step S908 is greater than the variance value V2 calculated in step S909. When the variance value V1 is greater than the variance value V2 (Yes in step S911), the processing advances to step S912. When the variance value V1 is less than the variance value V2 (No in step S911), the processing advances to step S913.

In step S912, the emotion determiner 233 determines the emotion E1 corresponding to the variance value V1 as the emotion Eresult of the user. The PC 200 then ends the procedure in FIG. 9.

In step S913, the emotion determiner 233 determines the emotion E2 corresponding to the variance value V2 as the emotion Eresult of the user. The PC 200 then ends the procedure in FIG. 9.

(Specific Operation Example)

FIGS. 10A to 10C show operation examples in the fourth embodiment. FIG. 10A shows an example temporal change of the score for each emotion (score based on the change in the facial expression) calculated by the first emotion estimator 231. In FIG. 10A, the emotion E1 (emotion estimated based on the change in the facial expression) is shown in bold frames. FIG. 10B shows an example temporal change of the score for each emotion (score based on the change in the temperature) calculated by the second emotion estimator 232. In FIG. 10B, the emotion E2 (emotion estimated based on the change in the temperature) is shown in bold frames. FIG. 10C shows an example temporal change of the emotion (emotion Eresult) determined by the emotion determiner 233.

In the examples in FIGS. 10A to 10C, both the emotions E1 and E2 are calmness for the period from frame 0 to frame 2, and calmness is thus determined as the emotion Eresult. For frame 3, the emotion E1 is anger, and the emotion E2 is calmness. The emotions E1 and E2 are different. For the emotion E1 (anger), the variance value V1 calculated from the four scores (22, 55, 12, and 11) calculated by the first emotion estimator 231 is 319. For the emotion E2 (calmness), the variance value V2 calculated from the four scores (52, 20, 8, and 20) calculated by the second emotion estimator 232 is 267. The variance value V1 (319) corresponding to the emotion E1 (anger) is greater than the variance value V2 (267) corresponding to the emotion E2 (calmness), and anger is thus determined as the emotion Eresult. Similarly in other frames, the emotion Eresult is determined based on, for example, the match or mismatch between the score for the emotion E1 and the score for the emotion E2, and on the relationship between the variance value V1 and the variance value V2.

(Overview)

In the fourth embodiment as described above, the highly accurate emotion determination can be achieved using the simple structure with high usability, as in the first embodiment. In addition, determining the emotion with the greater score variance value among multiple emotions of the emotion estimated based on the face image and the emotion estimated based on the temperature as the emotion of the user can yield a more reliable emotion as the determination result.

Fifth Embodiment

A fifth embodiment of the present invention will now be described.

(Structure)

The structure of the communication system according to the fifth embodiment is substantially the same as in the first embodiment. FIG. 11 is a block diagram of the PC 200 according to the fifth embodiment. In the fifth embodiment, the PC 200 also includes the image obtainer 210, the temperature obtainer 220, the controller 230, the storage 240, and the output unit 250 as in the first embodiment. However, the controller 230 in the fifth embodiment further includes an estimation result adjuster 234. In the fifth embodiment, the processing other than those described below are the same as in the first embodiment.

In the fifth embodiment, each of the first emotion estimator 231 and the second emotion estimator 232 stores (records, or specifically, accumulates) the estimation result of the emotion of the user into the storage 240.

The estimation result adjuster 234 adjusts the estimation result obtained by the first emotion estimator 231 and the estimation result obtained by the second emotion estimator 232 stored in the storage 240. For clarity, in FIG. 11, arrows from the first emotion estimator 231 and the second emotion estimator 232 point to the estimation result adjuster 234 instead of arrows for writing or reading estimation results in the storage 240. More specifically, the estimation result adjuster 234 detects a period when the variance value of the scores (estimated emotion scores) for the period preceding a predetermined time is less than a predetermined threshold value. Such a period can be determined as the period with a stable estimation result of the emotion of the user. The estimation result adjuster 234 then replaces the estimation result from a first period with the variance value less than the predetermined threshold value backward up to the period immediately after a second period with the variance value less than the predetermined threshold value with the estimation result in the first period. The estimation result adjuster 234 adjusts the estimation result obtained by the first emotion estimator 231 and the estimation result obtained by the second emotion estimator 232 to detect such a period and replace the estimation result. The estimation result adjuster 234 is an example of an adjuster in an aspect of the present invention.

The emotion determiner 233 determines the emotion of the user based on the adjusted estimation result obtained by the estimation result adjuster 234. For example, the emotion of the user is determined by any method described in the first to fourth embodiments.

In this manner, the emotional changes can be smoothed for detection of the tendency with high accuracy. This allows intended control with, for example, emotional changes being predicted. When, for example, the emotion of the user tends to change from anger to sadness, the behavior (e.g., speech) of the communication robot 30 can be controlled to communicate with an angry user while expecting that the emotion of the user may change to sadness.

(Specific Operation Example)

FIGS. 12A to 12C show operation examples in the fifth embodiment. An example process for adjusting the estimation result of the first emotion estimator 231 will now be described below. The estimation result of the second emotion estimator 232 is also adjusted in the same manner as described below.

FIG. 12A shows an example temporal change of the score before being changed by the estimation result adjuster 234, and an example temporal change of the score for each emotion (score based on the change in the facial expression) calculated by the first emotion estimator 231. In FIG. 12A, the emotion E1 (emotion estimated based on the change in the facial expression) is shown in bold frames.

First, the estimation result adjuster 234 calculates the variance value of the emotion E1 estimated by the estimation result adjuster 234 for the period up to a predetermined time based on the temporal change in FIG. 12A. The predetermined time is not limited, but is herein to be the time for three frames. For example, the emotion E1 (emotion with the greatest score) is calmness for frame 2. The estimation result adjuster 234 thus calculates the variance value (16.9) from the calmness score for frame 2 (56), the calmness score for frame 1 (50), and the calmness score for frame 0 (60). The emotion E1 (emotion with the greatest score) is anger for frame 3. The estimation result adjuster 234 thus calculates the variance value (251) from the anger score (55) for frame 3, the anger score (23) for frame 2, and the anger score (20) for frame 1. The estimation result adjuster 234 calculates the variance values for other frames in the same manner. FIG. 12B shows an example temporal change of the calculated variance values.

The estimation result adjuster 234 then detects the period (frame) with the variance value less than the predetermined threshold value. The predetermined threshold value is not limited, but is herein to be 50. In FIG. 12B, variance values less than the predetermined threshold (50) are shown in bold frames. More specifically, frames 2, 7, 13, and 14 are detected.

Finally, the estimation result adjuster 234 replaces the estimation result from the first period with the variance value less than the predetermined threshold value (50) backward up to the period immediately after the second period with the variance value less than the predetermined threshold value (50), with the estimation result in the first period. As described above, frames 2, 7, 13, and 14 are detected as periods with the variance value less than the predetermined threshold (50) in FIG. 12B. Thus, the estimation result adjuster 234 replaces the scores for frames 0 to 2 with the score for frame 2, the scores for frames 3 to 7 with the score for frame 7, and the scores for frames 8 to 13 with the score for frame 13. FIG. 12C shows an example temporal change of the score after being changed by the estimation result adjuster 234.

Although FIG. 12C shows the score for the emotion E1 alone (emotion estimated to be held by the user), the above replacement may be performed for scores other than the emotion E1. For a series of multiple frames with the same emotion E1, the scores may be replaced for matching the scores among the multiple frames. In FIGS. 12A to 12C, for example, both the emotions E1 for frame 13 and for frame 14 are sadness. The estimation result adjuster 234 may thus replace the scores for frames 8 to 14 with the score for frame 13 or frame 14.

(Overview)

In the fifth embodiment as described above, the highly accurate emotion determination can be achieved using the simple structure with high usability, as in the first embodiment. In addition, the result of the emotion estimation is adjusted to detect smoothed emotional changes for detection of the tendency with high accuracy.

Sixth Embodiment

A sixth embodiment of the present invention will now be described.

(Structure)

The structures of the communication system and the PC 200 according to the sixth embodiment are substantially the same as in the first embodiment. In the sixth embodiment, each of the first emotion estimator 231 and the second emotion estimator 232 estimate the emotion of the user in a first cycle. The emotion determiner 233 uses the estimation result obtained by the first emotion estimator 231 and the estimation result obtained by the second emotion estimator 232, updated in a second cycle that is longer than the first cycle. For example, the second cycle is three times the first cycle. When the frame rate of the image captured with the camera 10 is 30 fps, and the first cycle corresponds to the frame rate, the second cycle corresponds to ⅓ of the frame rate (10 fps). The structure (processing) other than these is the same as in any of the first to fourth embodiments.

This can reduce the frequency of the processing performed by the emotion determiner 233, for example, in updating the estimation result obtained by the first emotion estimator 231 and the estimation result obtained by the second emotion estimator 232 to reduce the processing load for the emotion determination. The emotion determiner 233 may perform the emotion determination and output the results in the first cycle or in the second cycle. When the determination and the output are performed in the second cycle, the processing load in the emotion determiner 233 can be reduced further.

(Specific Operation Example)

FIGS. 13A and 13B show operation examples in the sixth embodiment. An example process for the emotion determiner 233 updating the estimation result obtained by the first emotion estimator 231 will now be described below. The emotion determiner 233 also updates the estimation result obtained by the second emotion estimator 232 in the same manner as described below.

FIG. 13A shows an example temporal change of the score for each emotion (score based on the change in the facial expression) calculated by the first emotion estimator 231. In FIG. 13A, the emotion E1 (emotion estimated based on the change in the facial expression) is shown in bold frames.

FIG. 13B shows an example temporal change of the score for each emotion (score based on the change in the facial expression) used in the emotion determiner 233. In FIG. 13B, the emotion E1 (emotion estimated based on the change in the facial expression) is also shown in bold frames.

As shown in FIG. 13A, the first emotion estimator 231 calculates and updates the score for each frame. In contrast, as shown in FIG. 13B, the emotion determiner 233 updates the score every three frames. More specifically, the emotion determiner 233 also uses the score for frame 0 as the scores for frames 1 and 2. The emotion determiner 233 can thus perform the processing for frames 1 and 2 for a period preceding frames 1 and 2. In other words, the result of the emotion determination can be obtained more quickly. The score is updated for frame 3, and the score for frame 3 is also used as the scores for frames 4 and 5. After that as well, the score is updated in the same manner.

(Overview)

In the sixth embodiment as described above, the highly accurate emotion determination can be achieved using the simple structure with high usability, as in the first embodiment. In addition, reducing the frequency of updating the emotion estimation result used for the emotion determination can reduce the processing load for the emotion determination and increase the processing speed of the emotion determination (the time taken to obtain the emotion determination result can be reduced).

<Others>

The embodiments described above are mere examples of the present invention. The present invention is not limited to the embodiments described above, but may be modified variously within the scope of the technical ideas of the invention. The processing in the first to sixth embodiments may be combined as appropriate.

<Appendix 1>

An emotion determination device (100, 200), comprising: a first estimator (101, 231) configured to estimate an emotion of a user based on a change in a facial expression of the user detected from a face image of the user;

a second estimator (102, 232) configured to estimate the emotion of the user based on a change in a temperature of the user detected contactlessly from the user; and a determiner (103, 233) configured to determine the emotion of the user based on an estimation result obtained by the first estimator and an estimation result obtained by the second estimator.

<Appendix 2>

An emotion determination method, comprising:

(S302, S502, S702, S902) estimating an emotion of a user based on a change in a facial expression of the user detected from a face image of the user;

(S304, S504, S704, S904) estimating the emotion of the user based on a change in temperature of the user detected contactlessly from the user; and (S305 to S310, S505 to S513, S705 to S713, S905 to S913) determining the emotion of the user based on an estimation result in the estimating based on the change in the facial expression and an estimation result in the estimating based on the change in the temperature.

REFERENCE SIGNS LIST

100: Emotion determination device
101: First emotion estimator
102: Second emotion estimator
103: Emotion determiner
10: Camera
20: Temperature measurement device
30: Communication robot
200: PC (Emotion determination device)
210: Image obtainer
220: Temperature obtainer
230: Controller
240: Storage
250: Output unit
231: First emotion estimator
232: Second emotion estimator
233: Emotion determiner
234: Estimation result adjuster
241: First emotion estimation dictionary
242: Second emotion estimation dictionary

The invention claimed is:

1. An emotion determination device, comprising:
a memory configured to store computer-executable instructions; and
a processor configured to execute the computer-executable instructions stored in the memory to implement:
a first estimator configured to estimate an emotion of a user based on a change in a facial expression of the user detected from a face image of the user;
a second estimator configured to estimate the emotion of the user based on a change in a temperature of the user detected contactlessly from the user;
a determiner configured to determine the emotion of the user based on an estimation result obtained by the first estimator and an estimation result obtained by the second estimator; and
an adjuster configured to detect a period with a variance value, for the period up to a predetermined time, of scores indicating a likelihood of the user holding an estimated emotion being less than a predetermined threshold value and adjust the estimation result obtained by the first estimator and the estimation result obtained by the second estimator to replace an estimation result from a first period with the variance value less than the predetermined threshold value backward up to a period immediately after a second period with the variance value less than the predetermined threshold value with an estimation result in the first period,
wherein the determiner determines the emotion of the user based on the adjusted estimation result obtained by the adjuster.

2. The emotion determination device according to claim 1, wherein
each of the first estimator and the second estimator calculates a score indicating a likelihood of the user holding an emotion of a plurality of emotions, and
the determiner determines the emotion of the user based on a score for each of the plurality of emotions calculated by the first estimator and a score for each of the plurality of emotions calculated by the second estimator.

3. The emotion determination device according to claim 2, wherein
the determiner determines, as the emotion of the user, an emotion with a greatest score calculated by the first estimator matching an emotion with a greatest score calculated by the second estimator, and
the determiner determines, in response to the emotion with the greatest score calculated by the first estimator not matching the emotion with the greatest score calculated by the second estimator, the emotion of the user based on a score for each of the plurality of emotions calculated by the first estimator and a score for each of the plurality of emotions calculated by the second estimator.

4. The emotion determination device according to claim 3, wherein in response to the emotion with the greatest score calculated by the first estimator not matching the emotion with the greatest score calculated by the second estimator, the determiner determines, as the emotion of the user, an emotion with a greater calculated score for the emotion with the greatest score calculated by the first estimator and the emotion with the greatest score calculated by the second estimator.

5. The emotion determination device according to claim 3, wherein
in response to the emotion with the greatest score calculated by the first estimator not matching the emotion with the greatest score calculated by the second estimator, the determiner determines, as the emotion of the user, an emotion with a greater sum of a score calculated by the first estimator and a score calculated by the second estimator of the emotion with the greatest score calculated by the first estimator and the emotion with the greatest score calculated by the second estimator.

6. The emotion determination device according to claim 3, wherein
in response to the emotion with the greatest score calculated by the first estimator not matching the emotion with the greatest score calculated by the second estimator, the determiner determines, as the emotion of the user, an emotion with a greater score change amount of the emotion with the greatest score calculated by the first estimator and the emotion with the greatest score calculated by the second estimator.

7. The emotion determination device according to claim 3, wherein
in response to the emotion with the greatest score calculated by the first estimator not matching the emotion with the greatest score calculated by the second estimator, the determiner determines, as the emotion of the user, an emotion with a greater score variance value of the emotion with the greatest score calculated by the first estimator and the emotion with the greatest score calculated by the second estimator.

8. An emotion determination method, comprising:
estimating an emotion of a user based on a change in a facial expression of the user detected from a face image of the user;
estimating the emotion of the user based on a change in temperature of the user detected contactlessly from the user;
determining the emotion of the user based on an estimation result in the estimating based on the change in the facial expression and an estimation result in the estimating based on the change in the temperature;
detecting a period with a variance value, for the period up to a predetermined time, of scores indicating a likelihood of the user holding an estimated emotion being less than a predetermined threshold value; and
adjusting the estimation result in the estimating based on the change in the facial expression and the estimation result in the estimating based on the change in the temperature to replace an estimation result from a first period with the variance value less than the predetermined threshold value backward up to a period immediately after a second period with the variance value less than the predetermined threshold value with an estimation result in the first period,
wherein the determining determines the emotion of the user based on the adjusted estimation result.

9. A non-transitory computer readable medium storing a program for causing a computer to perform operations included in the emotion determination method according to claim 8.

10. An emotion determination device, comprising:
a memory configured to store computer-executable instructions; and
a processor configured to execute the computer-executable instructions stored in the memory to implement:
a first estimator configured to estimate an emotion of a user based on a change in a facial expression of the user detected from a face image of the user;
a second estimator configured to estimate the emotion of the user based on a change in a temperature of the user detected contactlessly from the user; and
a determiner configured to determine the emotion of the user based on an estimation result obtained by the first estimator and an estimation result obtained by the second estimator,
wherein, each of the first estimator and the second estimator calculates a score indicating a likelihood of the user holding an emotion of a plurality of emotions,
the determiner determines the emotion of the user based on a score for each of the plurality of emotions calculated by the first estimator and a score for each of the plurality of emotions calculated by the second estimator,
the determiner determines, as the emotion of the user, an emotion with a greatest score calculated by the first estimator matching an emotion with a greatest score calculated by the second estimator, and
the determiner determines, in response to the emotion with the greatest score calculated by the first estimator not matching the emotion with the greatest score calculated by the second estimator, the emotion of the user based on a score for each of the plurality of emotions calculated by the first estimator and a score for each of the plurality of emotions calculated by the second estimator.

11. The emotion determination device according to claim 10, wherein
each of the first estimator and the second estimator estimates the emotion of the user in a first cycle, and
the determiner uses the estimation result obtained by the first estimator and the estimation result obtained by the second estimator updated in a second cycle longer than the first cycle.

* * * * *